(12) United States Patent
Bruzzano et al.

(10) Patent No.: US 10,196,286 B2
(45) Date of Patent: Feb. 5, 2019

(54) METHOD FOR REMOVING FLUORINATED ORGANIC COMPOUNDS FROM CONTAMINATED FLUIDS, AND ADSORBENT COMPONENT AND ADSORBENT KIT USED THEREFOR

(71) Applicants: Fraunhofer-Gesellschaft zur Förderung der angewandten Forschung e.V., Munich (DE); Cornelsen Solutions GmbH, Essen (DE)

(72) Inventors: Stefano Bruzzano, Duisburg (DE); Martin Cornelsen, Bochum (DE)

(73) Assignees: Fraunhofer-Gesellschaft zur Forderung der angewandten Forschung e.V. (DE); Cornelsen Solutions GmbH (DE)

( * ) Notice: Subject to any disclaimer, the term of this patent is extended or adjusted under 35 U.S.C. 154(b) by 352 days.

(21) Appl. No.: 14/782,259

(22) PCT Filed: Apr. 3, 2014

(86) PCT No.: PCT/EP2014/056761
§ 371 (c)(1),
(2) Date: Oct. 2, 2015

(87) PCT Pub. No.: WO2014/161973
PCT Pub. Date: Oct. 9, 2014

(65) Prior Publication Data
US 2016/0046506 A1 Feb. 18, 2016

(30) Foreign Application Priority Data
Apr. 5, 2013 (DE) .................. 10 2013 206 066

(51) Int. Cl.
*C02F 1/28* (2006.01)
*C02F 1/52* (2006.01)
(Continued)

(52) U.S. Cl.
CPC ............... *C02F 1/285* (2013.01); *B01J 20/22* (2013.01); *C02F 1/52* (2013.01); *C02F 1/5272* (2013.01);
(Continued)

(58) Field of Classification Search
None
See application file for complete search history.

(56) References Cited

U.S. PATENT DOCUMENTS 5,336,420 A * 8/1994 Horodysky ........ C07D 285/125
252/402
2006/0009369 A1 * 1/2006 Kilkenny ................ A01N 33/12
510/504

(Continued)

FOREIGN PATENT DOCUMENTS

DE 39 08 491 A1 9/1990
DE 10 2011 114 952 A1 4/2013
(Continued)

OTHER PUBLICATIONS

International Search Report with English translation, dated Jun. 12, 2014, pp. 1-5, International Patent Application No. PCT/EP2014/056761, European Patent Office, Rijswijk, The Netherlands.

*Primary Examiner* — Clare M Perrin
(74) *Attorney, Agent, or Firm* — Brinks Gilson & Lione; Michael E. Hussey; Jonathan M. Hartley

(57) ABSTRACT

A method may be provided for removing fluorinated organic compounds from contaminated fluids by means of a kit that comprises a first and a second adsorbent component, or only by means of the first adsorbent component alone. The
(Continued)

second adsorbent component is a solid adsorbent; the first adsorbent component is a chemical compound that contains a lipophilic group and a hydrophilic group, or contains such a compound in dissolved form, wherein the hydrophilic group contains at least one cationic group and wherein the lipophilic group is selected from alkyl groups that comprise at least one octylene unit, from aryl groups, and from aralkyl groups. The contaminated fluid may be brought in contact with the first adsorbent component, and optionally the fluid is also brought in contact with the second adsorbent component. The adsorbent component(s) may be removed from the fluid together with the adsorbed fluorinated organic compounds.

17 Claims, 3 Drawing Sheets

(51) Int. Cl.
*C02F 1/68* (2006.01)
*B01J 20/22* (2006.01)
*C02F 1/58* (2006.01)
*B01J 8/00* (2006.01)
*C07C 211/64* (2006.01)
*C02F 101/36* (2006.01)

(52) U.S. Cl.
CPC .............. *C02F 1/583* (2013.01); *C02F 1/683* (2013.01); *B01J 8/00* (2013.01); *C02F 2101/36* (2013.01); *C02F 2301/08* (2013.01); *C07C 211/64* (2013.01)

(56) References Cited

U.S. PATENT DOCUMENTS

2008/0264864 A1* 10/2008 Dadalas .................... C08F 6/16
          210/656
2013/0023408 A1*  1/2013 Kambala ................ B01D 15/00
          502/401

FOREIGN PATENT DOCUMENTS

EP          1 561 729 A1    8/2005
WO   WO 2011/069189 A1     6/2011

* cited by examiner

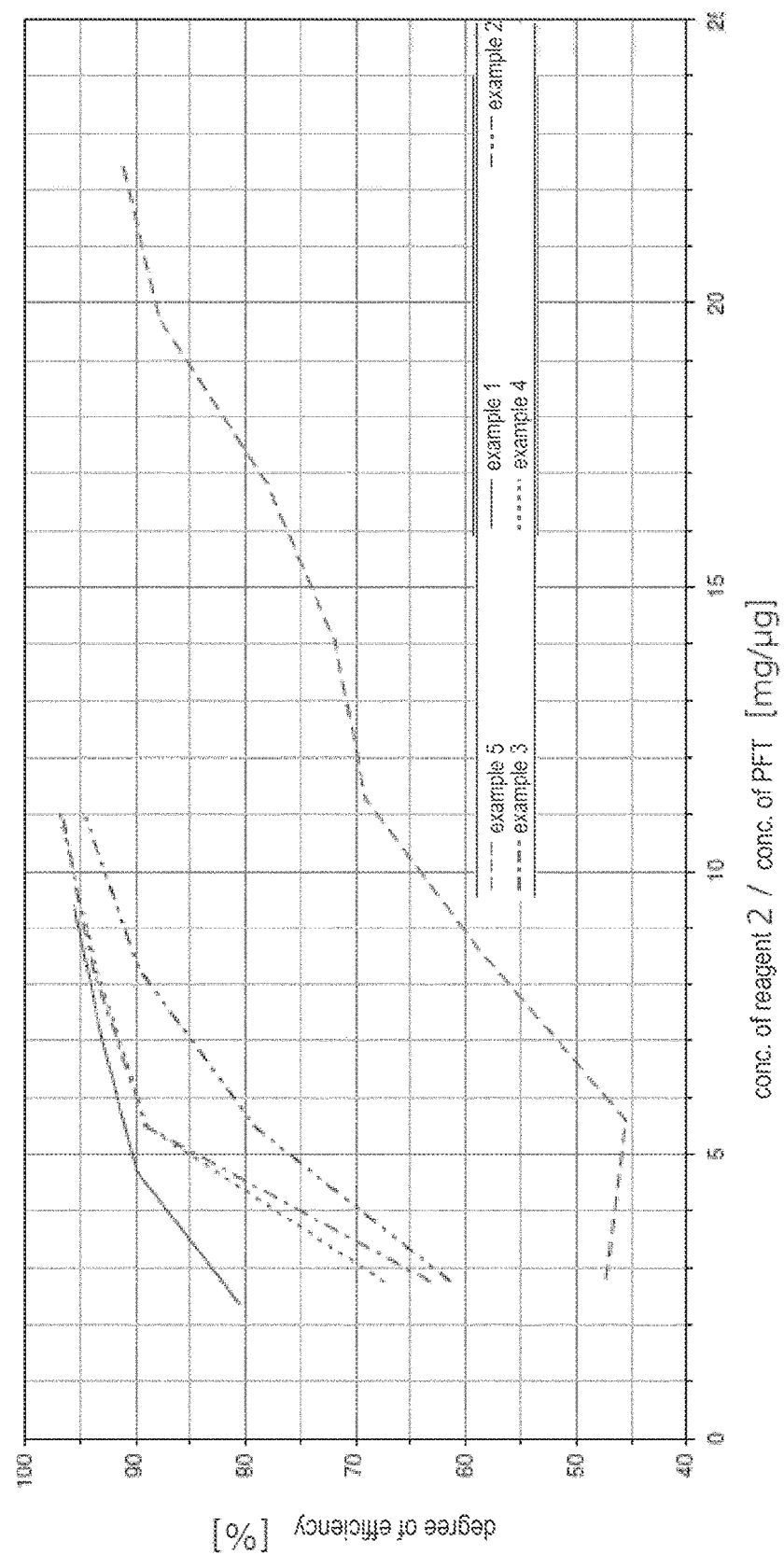

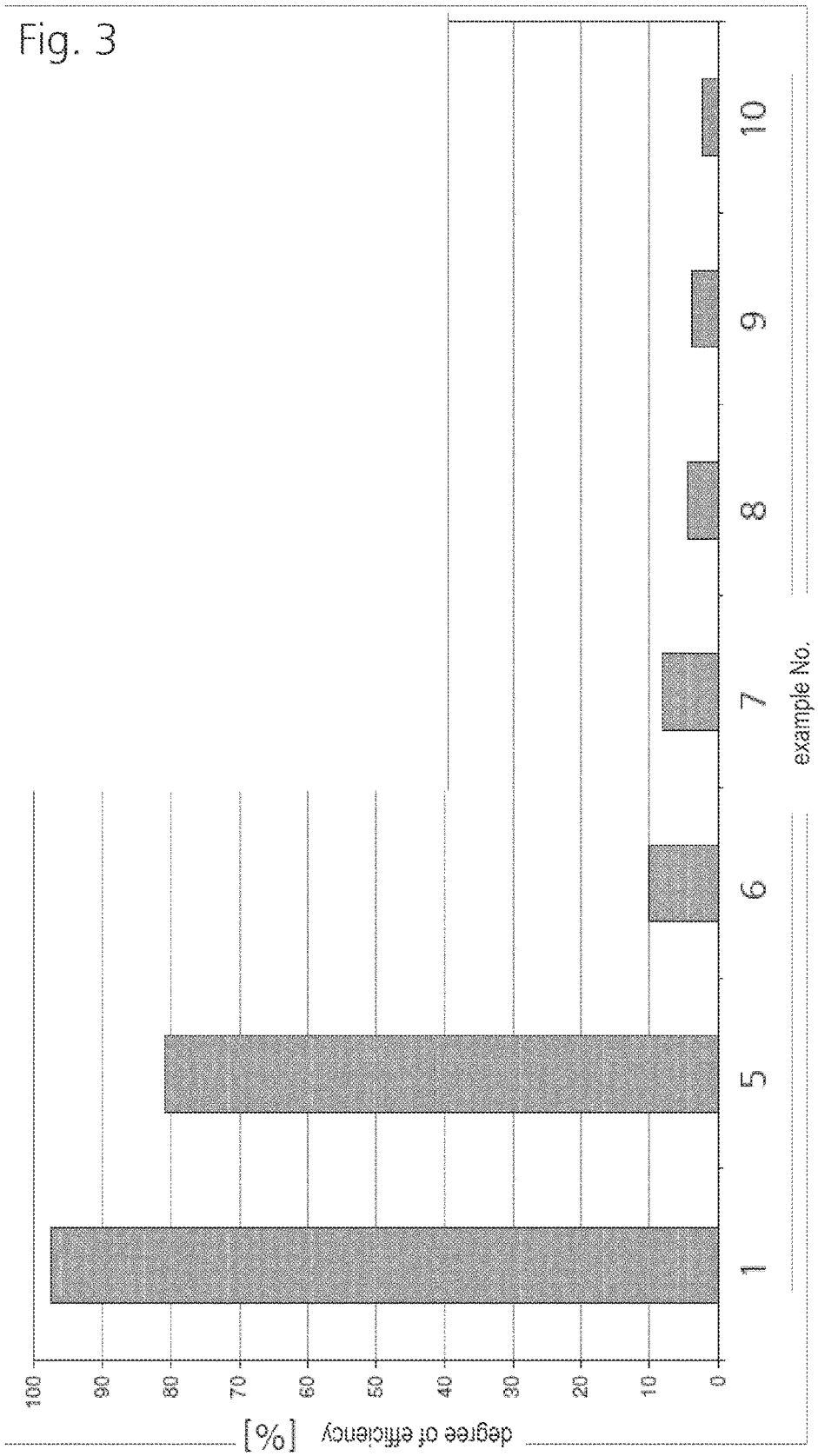

METHOD FOR REMOVING FLUORINATED ORGANIC COMPOUNDS FROM CONTAMINATED FLUIDS, AND ADSORBENT COMPONENT AND ADSORBENT KIT USED THEREFOR

CROSS-REFERENCE TO RELATED APPLICATIONS

This application is a 371 nationalization of PCT/EP2014/056761, entitled "METHOD FOR REMOVING FLUORINATED ORGANIC COMPOUNDS FROM CONTAMINATED FLUIDS, AND ADSORBENT COMPONENT AND ADSORBENT KIT USED THEREFORE," having an international filing date of Apr. 3, 2014, the entire contents of which are hereby incorporated by reference, which in turn claims priority to German patent application DE 102013206066.1 filed on Apr. 5, 2013, entitled "Verfahren zur Abtrennung fluorierter organischer Verbindungen aus kontaminierten Fluiden und hierfür verwendetes Adsorbens-Kit," the entire contents of which are hereby incorporated by reference.

BACKGROUND

The application relates to a method, which is particularly suitable for the separation of fluorinated organic compounds from fluids, a kit that is used therefore, and an especially soluble first adsorbent component with a lipophilic group and a hydrophilic group that can be used therefore. In this connection, on the one hand, the contaminated fluid comes into contact with at least the first, as a rule amphiphilic, adsorbent component. There can then be a contact with a second solid adsorbent component, which makes possible a adduct formation, so that the loaded adsorbent material can be separated from the purified fluid. Fluorinated organic compounds have excellent and unique technological properties, which is why they have long been utilized in many different industrial products and processes (for example, as textile and paper finishes, as water and dirt repellent coatings, as hydraulic fluids, as fire extinguishing foams, in the production of Teflon as well as in electroplating). Owing to their specific properties, there are frequently no alternatives to these substances.

Fluorinated compounds, in particular perfluorinated surfactants, are, however, potentially toxic to the environment as well as to humans, which is a result of the high tendency to bioaccumulation. Perfluorinated surfactants have in recent years been ubiquitously found in the environment because of their high persistence. They are basically released to the environment via wastewater from the production processes of fluorochemical products, or as a result of the use and release of the corresponding products to the environment. By way of example, perfluorinated surfactants, such as foaming agents in fire extinguishing foams as well as humectants and antifogging agents in the electroplating, photography or semiconductor industries, should be mentioned.

The provisions and guidelines and regulations of many countries, for example, the European Directive 2006/122/EG have drawn attention to the dangers of perfluorinated octanoic acid and perfluorinated sulfonic acids and their use has been greatly restricted.

Perfluorinated surfactants are, however, indispensable in a series of industrial processes, in particular in electroplating, in fire protection as well as in photography and in semiconductor technology; exceptions for those applications have therefore been incorporated in the latest legal regulations. These substances are used, for example, in occupational safety in electroplating technology (antifogging agents and humectants); they are used as a foam barrier or liquid fume suppressant for the immobilization of the very harmful and carcinogenic chromic acid.

Different provisions have currently been implemented in plants in order to reduce the discharge of fluorinated organic compounds, in particular highly toxic compounds, such as special perfluorinated surfactants (PFS), into wastewater and ground water. The separation and separate disposal of the wastewater substreams loaded with these components should be particularly mentioned. The use of various treatment methods for wastewater and ground water purification is of particular importance for this purpose.

During purification, however, the problem is that, due to their chemical and physical properties, perfluorinated surfactants can, in particular, not be effectively separated from contaminated fluids, either with conventional biological methods or by means of classical physical methods, such as stripping.

US 2007/01381-10 describes, for example, the separation of perfluorinated surfactants by means of capacitive deionization of contaminated water. This method is, however, too cost intensive with regard to procurement, operation and maintenance of the plants for the purification of large amounts of wastewater. This likewise applies to wet oxidative methods, for example, by means of UV, ozone, peroxide or microwave irradiation. In some physical separation methods, such as membrane technology, highly concentrated aqueous solutions are left as waste, whose (thermal) disposal is difficult and thus uneconomic.

The chemical separation methods in particular include adsorption methods. Adsorbent resins, for example, are used for the purification of wastewater. They have a very selective adsorption capability and a great absorptive capacity with respect to high pollutant concentrations. WO 2008/066748 A1 discloses, for example, the use of ion exchangers. Nevertheless, the adsorbent resins could not gain acceptance as adsorptive materials for the conditioning of wastewater and ground water. They are comparatively more expensive than activated carbon and their regeneration is more complex.

Adsorption on activated carbon is therefore frequently used for the purification of wastewater containing PFS. Fluorinated surfactants, in particular short-chain perfluorinated surfactants, can, however, not be selectively separated herewith.

EP 1 561 729 A1, for example, discloses an adsorption method based on activated carbon for separating fluorinated emulsifiers in wastewater containing particles of fluoropolymers. Non-ionic or anionic surfactants are added to the wastewater for this purpose in order to prevent the deposition of polymer particles on the activated carbon and a consequent clogging of the filter.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

FIG. 2 illustrates applying the achieved degree of efficiency level depending on the ratio of adsorbent and PFT adsorbent; and FIG. 3 illustrates achieved degrees of efficiency of examples 1 and 5 to 10 depending on a solid adsorbent component.

DETAILED DESCRIPTION

Figure 1:
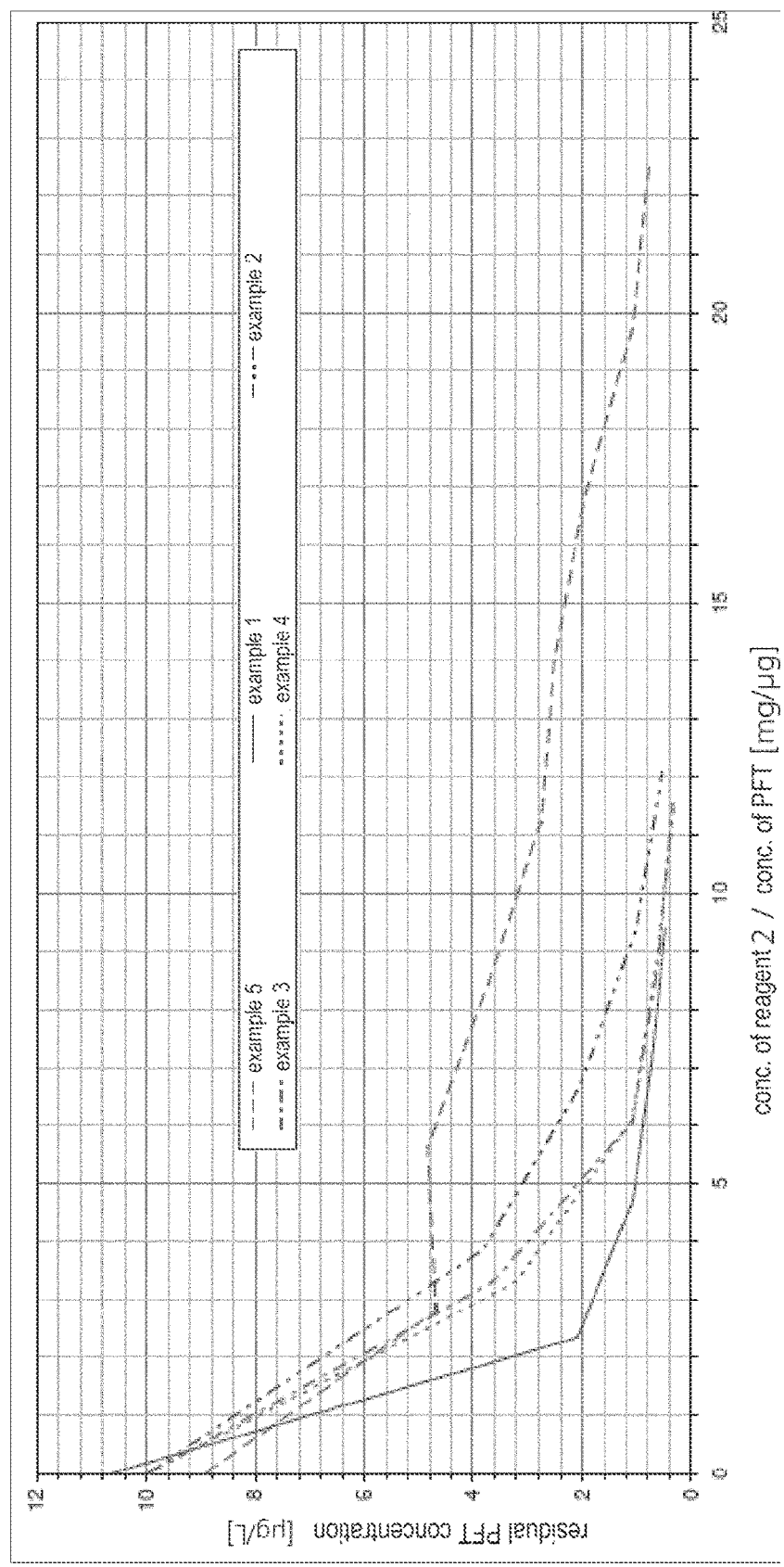
FIG. 1 illustrates results obtained from a test series of Table 1.

It is thus the object of the present invention to overcome the disadvantages of the prior art and disclose adsorption means and a method for the use of additives for the separation of fluorinated organic compounds, in particular fluorinated or perfluorinated surfactants, from contaminated fluids, which overcome the disadvantages of the prior art.

According to the present invention, it has been found that fluorinated organic compounds can be removed from fluids by means of a kit comprising a first adsorbent component and a second adsorbent component; this, in particular, concerns the separation of perfluorinated organic compounds and/or fluorinated surfactants from fluids contaminated therewith. In some embodiments, using only the first adsorbent component will, however, be sufficient to separate those substances.

The first adsorption component is a chemical compound containing a lipophilic group and a hydrophilic group (and thus an amphiphilic chemical compound), wherein the hydrophilic group contains at least one cationic group.

The chemical compound that contains a lipophilic group and a hydrophilic group can be present as a liquid or also as a solid under normal conditions and can be brought into a dissolved form to be used in the method according to the present invention (for example, by means of a solubilizing agent; the formation of a solution in the fluid to be purified is sufficient for this purpose. In this case, dissolved form is also understood to mean that at least one percentage by weight of the first adsorbent component, which corresponds to 10% of the percentage by weight of the fluorinated organic compound present in the contaminated fluid, is present in dissolved form in the contaminated fluid. Complete dissolution will, however, frequently occur. According to the present invention, the micelles formed in the fluid will also always be included in the dissolved form. The solubility can, therefore, be easily established via the determination of the amount of undissolved first adsorbent component. In the case of a solution for the method according to the present invention, a first adsorbent component in which the amphiphilic chemical compound is present dissolved in a solvent, or can be dissolved, for example, in an aqueous fluid to be purified can thus be used.

Lipophilic group in the first adsorbent component is understood to mean that at least one of the following groups is contained as a structure: an alkyl group comprising at least one octylene unit (that is, one unit having the formula —$C_8H_{16}$—, that is, an octyl radical or a non-terminal alkyl group, for example, an octylene group substituted with the hydrophilic group), or, as an alternative, an aryl group or an aralkyl group.

The first adsorbent component to a certain extent can function as a carrier connection owing to the specific structural configuration of said component; the adjustment of the interactions between the additive and the fluorinated organic compound can be customized for the substances to be separated, so that an adduct is formed, which can be subsequently separated by means of the second adsorbent component, or which already precipitates from the fluid to be purified without adding the second adsorbent component (wherein precipitation according to the present invention, beside a sedimentation, is understood as also meaning, in particular, flocculation and flotation). For the first adsorbent component, a series of simple starting materials, for example, commercially available surfactant structures, which are especially known to the person skilled in the art from general chemistry and from areas like detergent, paper, food and water chemistry, can be resorted to.

The optional second adsorbent component is a conventional solid adsorbent, that is, a substance that, due to its large, active surface, can selectively concentrate (that is, adsorb) chemical compounds to be separated from gaseous or liquid mixtures on their boundary surface. The second adsorbent component is therefore also frequently called "solid component" according to the present invention. In particular, adsorbents that are also suitable as a stationary separation phase, and with which the separation of fluorinated compounds can be carried out, in particular fluorinated surfactants can be used as a second adsorbent components. Such adsorbents have for long been known to the person skilled in the art. According to the present invention, it has been observed that the effect of the solid adsorbent component can be supplemented or reinforced by the first adsorbent component.

With reference to the first adsorbent component, solid is understood to mean that said component does not dissolve in the contaminated fluid. The same also applies to a possibly present solvent, which is required for the conversion of a solid amphiphilic chemical compound into the liquid state, that is, for making available a first adsorbent component. The solid adsorbent component does not dissolve in such a solvent either.

The aforementioned object is therefore attained by means of the following method according to the present invention utilizing the first adsorbent component:

In step A), the first adsorbent component is first made available. In step B), the contaminated fluid is subsequently contacted with the first adsorbent component. The at least first adsorbent component with the adsorbed fluorinated organic compounds is finally separated from the fluid in step D).

According to the present invention, it has been determined that a very selective separation of fluorinated organic compounds, in particular fluorinated or perfluorinated surfactants, is possible by means of such a method by contacting a contaminated fluid with a carrier compound, namely the first adsorbent compound. Without desiring to be limited thereto, it is assumed that this observation is based on the following model representation:

In step B), the fluorinated organic compound to be separated interacts with the first adsorbent component, wherein the interaction between the two substances is so strong that the first adsorbent component can also be designated as carrier compound. If the concentration of the first adsorbent component in the fluid is selected large enough, then micelles of the amphiphilic first adsorbent component can advantageously be formed; the fluorinated organic compound to be separated can then possibly arrange itself in the interior of the micelle. The first adsorbent component is further selected in such a way that it either precipitates from the fluid by forming an adduct with the substances to be separated as a result of its solubility properties, or is precipitated after forming an adduct by the addition of the second adsorbent component.

In step D), the adduct can finally be separated from the contaminated fluid with the amphiphilic first absorbent component and fluorinated organic compound, or with the second adsorbent component and fluorinated organic compound in the case of the embodiment described below. This is possible, for example, by sedimentation or filtration.

With the method according to the present invention, with the first adsorbent component as well as with the kit of first adsorbent component and second adsorbent component, a method is now made available with which the fluorinated organic compounds, in particular perfluorinated surfactants, can be economically separated from contaminated fluids. By means of the interaction of the amphiphilic chemical compound via the lipophilic groups, on the one hand, and the available cationic charge, on the other hand, an adduct results, which either precipitates on its own, at least, however, shows better adsorption on the solid adsorbent component (for example, activated carbon) than the pure fluorinated organic compound.

It has also been shown that the method according to the present invention is not exclusively suitable for the separation of perfluorinated or partially fluorinated surfactants, but also for perfluorinated compounds in general (which can be adequately separated due to the interaction with the hydrophobic groups), as well as of other fluorinated organic compounds (such as, for example, organic compounds with fluorinated alkyl groups or fluorinated aromatic compounds, which can in turn be more easily adsorbed by means of the hydrophobic groups). Fluoroalkyl alkanols or fluoroalkyl alkandiols, fluorotelomers, fluoroacrylates, fluoromethacrylates, fluoroalkyl dimethyl betaines, perfluorinated and partially fluorinated fatty acid esters, perfluorinated and partially fluorinated fatty alcohol sulfates, perfluorinated and partially fluorinated fatty alcohol polyglycol ether sulfates, nonionic polymer fluorinated surfactants, aliphatic partially fluorinated polymer esters and perfluoroalkyl betaines should be particularly mentioned.

The method according to the present invention is likewise suitable for the separation of other undesirable substances from fluids, in particular anionic substances, which can interact with a possibly contained cationic group and can thus be separated. Uranyl compounds or also inorganic or organic arsenates and antimonates should be especially mentioned in this regard.

The method according to the present invention, the first adsorbent component and the kit according to the present invention are finally not only suitable for the purification of contaminated water, but also of other liquids, such as organic solvents (unless there is a chemical reaction of the solvent with substituents of the first adsorbent component). The purification of gases, in particular of air, is furthermore basically also possible, but the process control is clearly more difficult than that of fluids owing to a multistep adsorption process. The first adsorbent component and the kit according to the present invention can also be used, if need be, for concentrating materials, for example, in particular expensive fluorine-containing compounds; such materials can subsequently be recovered in a desorption process.

As outlined above, the first adsorbent component used according to the present invention contains a lipophilic group. The latter comprises either an alkyl group, an aryl group and/or an aralkyl group. The alkyl group can be an octyl unit or contain an octylene unit. The lipophilia can be further increased with still longer alkylene and/or alkyl groups, which can be advantageous in the case of specific fluorinated organic compounds that are to be separated. A decylene unit or decyl unit or a decyl unit or dodecyl unit, for example, can be used as a lipophilic group. Phenyl groups or phenylene groups are especially taken into consideration as aryl groups, which phenyl groups are unsubstituted or can also be substituted (in this case, in particular, also in turn with other pure hydrocarbons in aromatic or aliphatic form). Benzyl groups are, for example, taken into consideration as aralkyl groups. The aralkyl groups, for example, the benzyl or benzylene groups, can be substituted or unsubstituted. Benzylene groups, in which the ionic group is bonded to the aromatic ring, are also conceivable. The alkyl group, aryl group or aralkyl group can likewise be partially fluorinated or perfluorinated in order to reinforce the interaction with the fluorine-containing compounds to be adsorbed. In this connection, partially fluorinated or perfluorinated alkyl or alkylene units should particularly be mentioned within these groups.

In order to already achieve a precipitation of the first adsorption component from the fluid by forming an adduct with the substances to be separated the first adsorbent component should be particularly selected so that—depending on the fluorine-containing compound—an adduct having a low water solubility results. This is basically already achieved by means of the said alkyl, aralkyl or aryl groups. This effect can, however, be further reinforced, if (referred to the fluorine-containing compounds to be separated) the equimolar amount of the first adsorbent component (also at concentrations of less than 1 µmol/l) is not already completely soluble in the fluid without a solubilizing agent. Independently thereof, compounds having at least two alkyl, aralkyl or aryl groups according to the definition of the preceding paragraph and/or an alkyl radical with at least one tetradecylene unit, but in particular compounds containing at least two groups with tetradecylene units, are also suitable for reinforcing these properties.

Within the scope of this application, a "cationic group" of the first adsorbent component should in general be understood in such a way that, in a given fluid, this group is always cationic or alternatively only present as a cation under specific conditions. In particular, in the case of aqueous fluids, the cationic group can therefore be present in neutral form at higher pH values and only at least partially in protonated form at lower pH values, as is frequently the case in primary, secondary or tertiary amines. It is important then that the cationic group is to a certain extent also present in protonated form in a given contaminated fluid. Primary, secondary and tertiary low molecular amines thus have a $pk_B$ of approx. 4 in water. As a rule, the protonated form is therefore predominantly present in pH neutral water. Only in highly alkaline water can the protonated portion be significantly lower. It should however be at least 1%, preferably at least 10%. A pretreatment of the contaminated water, in which the pH value is lowered, can then be carried out with such cationic groups in order to achieve a more effective adsorption.

According to the present invention, the cationic group contained in the first adsorbent component can in particular be an ammonium ion, usually an organic substituted ammonium (wherein the hydrophobic group frequently functions as "organic substituent" of the ammonium), but can also be a primary, secondary or tertiary amine. Quaternization can potentially occur in a modification reaction in primary, secondary or tertiary amines, so that at least partially quaternized amine groups are formed. The cationic group can furthermore also be a phosphonium ion, and, in this case, in particular an organic substituted phosphonium (in which, as a rule, the hydrophobic group is again used as an organic substituent). The cationic group can finally also be present as a metal complex, for example, a transition metal complex (in this case, a linkage to the hydrophobic group can likewise be present in the metal complex, wherein a number of possibilities is provided; the hydrophobic group can be, for example, a component of a ligand of the metal complex or also the ligand itself). In individual cases, the cationic group can also be present in a zwitterionic compound, for example, in a betaine structure (carbo-betaine and sulfo-betaine should especially be mentioned here, and namely with an ammonium group as a cation). As a rule, the purely cationic, that is, the non-zwitterionic structures, have however shown to be more advantageous.

If an organic substituted ammonium or amine is present as a cationic group, then one of the substituents is at the same time frequently the lipophilic group or contains the lipophilic group. Alkyl groups, for example, methyl, ethyl or n- or i-propyl groups are frequently present as further organic substituents.

Undesirable compounds, such as surfactants, but also anionic inorganic groups such as uranyl groups, can be adequately separated by means of such cationic groups.

According to another embodiment, the fluorinated organic compounds are separated from contaminated fluids by means of a kit consisting of a first and a second adsorbent component. The second adsorbent component, which is a solid adsorbent material, is then additionally made available in step A). The method further comprises step C), in which the fluid enters into contact with the second adsorbent component.

According to the present invention, it has been established that a still more selective separation of fluorinated organic compounds, in particular fluorinated or perfluorinated surfactants, is possible by means of the method according to this embodiment, namely by combining the solid adsorbent component with the first adsorbent component. In the case of first adsorbent components that do not already precipitate as an adduct with the fluorinated compounds, separability is only achieved by means of the addition of the second adsorbent component.

The contaminated fluid is brought into contact with the solid adsorbent component in step C), so that the adduct formed from the first amphiphilic adsorbent component and the fluorinated organic compound, on the one hand, and the potentially present portions of free fluorinated organic compound that are not bonded to the first adsorption component can be bonded to the surface of the second adsorbent component.

According to another embodiment, the method according to the present invention is carried out in such a way that steps B) and C) are implemented simultaneously, or that step B) is carried out prior to step C). From the above-described theoretical basic principles it arises that, as a rule, the adsorption of the fluorinated organic compound to be separated occurs first, and the adsorption of the adsorption product of step C) on the solid adsorption component, which has in particular not precipitated from the fluid, only occurs subsequently. In this respect, based on the theoretical considerations, it results that, as a rule, step B) must be carried out prior to step C). An implementation of step C) after step B) is less advantageous, as the risk exists that the first adsorbent component has already interacted with the second adsorbent component and the interaction with the fluorinated organic compound to be separated is thus made more difficult.

According to another embodiment, the method according to the present invention is implemented in such a way that a compound having the formula $R^1$-E-L-X, $R^1$-L-E-X or $R^1$-E-X is made available as a first adsorbent component in step A). In this connection, $R^1$ represents the lipophilic group, E represents the hydrophilic group, L represents a linker and X represents a reactive functional group. This reactive functional group X is selected in such a way that it undergoes a chemical reaction with the fluid or can form hydrogen bridges therewith in step B) and/or step C). Based on the fact that the contaminated fluid is predefined (frequently an aqueous liquid), it already becomes clear to the person skilled in the art which of such functional groups are suitable therefore based on the simplest organic chemistry considerations. The linker L can be any group that does not fall within the scope of the definition of the hydrophilic group, of the lipophilic group or of the reactive group. Alkylene groups (for example, $CH_2$ or $C_2H_4$) between E and X or ester or ether groups between $R^1$ and E are conceivable.

According to another embodiment, the functional group X, in particular in the case of an aqueous solvent, can have one, two or several hydroxy groups. In this way, the formation of hydrogen bridge bonds to the fluid is supported, and the hydrophilic properties of the hydrophilic groups are increased at the same time. An increase of the hydrophilic properties can be advantageous in individual cases.

The functional group X can further be selected in such a way that one, two or several hydroxy groups are formed by reaction with the fluid, in particular in the case of an aqueous solvent. The duration of this reaction can, however, exceed by far the duration of the method according to the present invention—depending on the group and milieu conditions— so that at best a partial conversion should be assumed here. According to another embodiment, the functional group X can therefore be selected from among epoxide groups and groups that react to a hydroxy group in an $S_N$ reaction in step B) and/or step C). In particular 2-chloroethanol groups, alkyl sulfonate groups, bromoalkyl groups or iodoalkyl groups should be mentioned as groups that react to a hydroxy group in an $S_N$ reaction.

According to another embodiment, the first adsorbent component is selected in such a way that two or more X or X-L groups are bonded to the hydrophilic group in the $R^1$-E-L-X, R1-L-E-X or $R^1$-E-X formula. Accordingly, the $R^1$-E-(L-$X_n$), $R^1$-E-(L-X)$_n$, $R^1$-L-E-X or $R^1$-E-$X_n$ formulas are in particular obtained. In this connection, n can then be two or three, but it can also be greater than 3 in the case of the first mentioned compound; L and X can be respectively equal or also different.

If several of such groups X are present, then X can be an ether group bonded via a methylene, ethylene or propylene linker, in particular an ethyl or methyl ether group. The same effect as with a single polyol substituent can be achieved with such multiple substituents.

Furthermore, at least two alcohol groups or precursors can be present as X groups, from which alcohol groups can be formed by reaction with the fluid. Vicinal diol groups or precursor structures should be particularly mentioned for this purpose in this connection.

According to another embodiment, the functional group X of the first adsorbent component is selected in such a way that properties that are dependent on time and method can be adjusted with it, in particular in the form of a pH regulator. Mineral acids are thus released, for example, with $S_N$ reactions of the group X in the case of 2-chloroethanol groups, alkyl sulfonate groups, bromoalkyl groups and iodoalkyl groups. This release occurs in situ, so that the "quaternization reagent" $H^+$ required for quaternizing the nitrogen and better adsorption of the fluorinated organic compound, for example, in the case of amines as a hydrophilic group, is generated locally. The milieu conditions of an aqueous mixture to be purified can furthermore also be changed by changing the pH value, so that the interaction of the adduct of the first adsorbent component and fluorinated organic compounds, on the one hand, and of the second adsorbent component, on the other hand, are reinforced.

The embodiments of the preceding seven paragraphs do not exclusively refer to the case in which compounds having the $R^1$-E-L-X, $R^1$-L-E-X or $R^1$-E-X formula are provided as a first adsorbent component. They also basically apply if compounds having the X-L-$R^1$-E or X-$R^1$-E formula are present. It has, however, proven to be advantageous, if the reactive X group, by means of which, among other things, the hydrophilic properties can be increased, is not bonded to the lipophilic but to the hydrophilic group.

According to another embodiment, the first adsorbent component is selected in such a way that it has a particularly low aquatic toxicity. The basically well suited quaternary non-polymer alkyl amines (for example, hexadecyl trimethyl ammonium chloride, dioctyl dimethyl ammonium chloride or quaternary coco alkyl methyl amine ethoxylate methyl chloride) and chloroalkylamines (for example, 3-chloro-2-hydroxypropyl-lauryl-dimethyl ammonium chloride) frequently have a high aquatic toxicity and are very toxic to aquatic organisms according to the CLP Directive 1272/2008. Aminopropyl esters and aminopropyl amides (for example, undecyl-amido-propyl-trimethyl ammonium methosulfates, docosylamidopropyl dimethylamine or 2-hydrox-3-trimethyl ammonium propyl docosanoate). Amino dipropionate (for example, 3-[2-carboxyethyl(octyl)amino]propionic acid or sodium octyl imino dipropionate), quaternary polymer alkyl amines (for example, diquaternary polydimethylsiloxane Rewoquat SQ1 from Evonik) already have a significantly lower toxicity. With regard to the toxicity, compound classes that are also used, for example, in hair shampoos or softeners are, however, the most advantageous. Betaine (for example, TEGO betaine F50 from Evonik), and in particular triethanol ester-quats (for example, dioleoyl ethyl hydroxy ethylmonium methosulfate or analogous compounds, in which the oleyl units at least in part are replaced by saturated C15 to C18 alkyl groups) should be mentioned.

A solid adsorbent component having a non-ionic surface is provided in step A) according to another embodiment. This should be understood to mean a surface on which temporary charges can in fact be temporarily present, possibly because it is an electric conductor with graphite structural elements, but on whose surface no durable ionic centers are present. Activated carbon, for example, whose surface can in fact be in part negatively charged, but of which it is known that it is not a compound with a ionic structure, should be mentioned.

The solid adsorbent component can, in particular, be a modified or unmodified adsorbent selected from among activated carbon, aluminum oxides, silica gels, soot, zeolites, silica gels, clays and fibrous or microcrystalline celluloses (such as bead-shaped celluloses). In order to achieve a better adsorption of the adduct from a fluorinated organic compound and first adsorbent component, the surface of the solid adsorbent component should possibly be lipophilic. The aforementioned solid adsorbent components can be lipophilically modified for this purpose; as an example of this, lipophilically modified aluminum oxides and hydrophobically modified bead-shaped celluloses should be mentioned.

The second adsorbent component preferentially has the largest possible specific surface (which can be determined by means of DIN ISO 9277:2003-05) with regard to its property as a conventional solid adsorbent. As a rule, the specific surface will be at least $10^1$ m$^2$/g and in particular between $5*10^2$ and $5*10^3$ m$^2$/g, for example, $9*10^2$ to $1.5*10^3$ m$^2$/g.

According to another embodiment, the second adsorbent component has an average particle diameter of 0.005 to 6 mm, in particular 0.02 to 4 mm, for example, 0.05 to 1 mm. In this case, the particle size is determined by means of screening processes. The particle can have any shape, for example, spherical or also needle-shaped. The shape of the porosity of the adsorbent can be freely selected from macroporous to microporous.

According to a further embodiment, the method according to the present invention can be carried out in such a way that a flocculant is added prior to step D) and usually also after step C) as well as after step B)) (in some cases, the addition can however also be made at the same time with, or prior to, step B) and/or step C), possibly because flocculation only occurs after the contaminant has been adsorbed). Such a method can basically be appropriate with very small particle sizes of the solid adsorbent component and advantageous with the larger surfaces associated with these particle sizes (the ranges mentioned in the preceding paragraph are thus valid in particular with regard to the upper limit). Adsorbents with average particle sizes of 0.005 mm up to a maximum of 1 mm, for example, up to a maximum of 0.5 mm of particle diameter, are particularly suitable for this embodiment. The solid adsorbent component is usually added in a finely distributed form to the contaminated fluid, so that adsorption can occur. The loaded adsorbent kit is then brought into flocculation with a flocculant. In this way, large flakes loaded with contaminant are generated, which easily sediment or float and/or can be separated by means of filtration. The amount of separated organofluorine compounds can be additionally increased by selecting a suitable flocculant. Cationic, but in particular also anionic polyelectrolytes are, for example, suitable as flocculants. They can be based, for example, on polyacrylate, polyacrylamide, polyethyleneimine and polyethylene oxides. Non-ionic synthetic and natural flocculants (for example, starch and glue) or inorganic polymers, such as polyaluminum compounds, also in combination with polyvalent, low molecular aluminum or iron salts can also be used.

The use of the adsorbent kit according to the present invention in combination with a flocculant has the advantage that the flocculation products containing the organofluorine compounds (for example, PFT-containing flocculation products) usually have a stable structure; the contaminant is then permanently immobilized in the flake and does not tend to wash out.

According to another embodiment, the method according to the present invention is carried out in such a way that a non-ionic surfactant is used in addition to the first adsorbent component, and namely, in particular, together with the first adsorbent component and in particular in step B). The formed adduct and/or the formed micelles can be stabilized in specific combinations of the first adsorbent component and the organofluorine compound by means of such a non-ionic surfactant. As a result, the efficiency can also be increased by means of such a co-surfactant. As non-ionic surfactants (oligo)oxyalkylene compounds (for example, fatty alcohol polyglycol ethers), carbohydrate compounds (for example, alkyl polyglucosides, saccharose esters, sorbitan esters and fatty acids N-methyl glucamides) and amino oxides (for example, alkyl dimethyl amino oxides) should be mentioned.

According to another embodiment, the method according to the present invention is carried out in a stirred tank reactor or under conditions corresponding to those in a stirred tank reactor. The method according to the present invention can realize its advantages particularly well under these conditions.

According to the present invention, it is namely not absolutely necessary that the contaminated fluid be guided via a column with the adsorbents. Instead, it will be sufficient if the two adsorbent components are brought into contact with the fluid in some way, and the adsorbent components and the fluid are then thoroughly mixed. Owing to the strong interactions between the fluorinated organic compound and the adsorbent components, such a thorough mixing, possibly in a stirred tank reactor, will be quite sufficient to ensure a good separation of the fluorinated organic compounds. It can, however, be appropriate to add a flocculant (which would not be necessary in a column or a separation column) in order to make possible a particularly fast separation. The method according to the present invention can, however, be basically carried out not only in a stirred tank reactor (in which the solid adsorbent component is frequently used in powdered form) but also in a column or in a fixed bed adsorber (in which the solid adsorbent component is frequently used in granulated form).

The method according to the present invention will be described in more detail below without intending to limit the disclosure to these descriptions:

After making available the components according to step A), an amphiphilic cationic additive is first added (as a first adsorbent component) to the contaminated fluid, from which the fluorinated organic compounds are to be removed, while stirring (~100 rpm). A compound provided with amino groups and/or quaternary ammonium groups and furthermore furnished with long alkyl chains (for example, cocoalkyl, stearyl or also octyl or dodecyl) for the lipophilic portion is selected in order to adjust a suitable hydrophobic/hydrophilic balance. Functionalities, such as aryl and benzyl groups, likewise make possible the desired interaction and formation of adducts with fluorinated organic compounds. Said aryl, aralkyl and alkyl groups can at the same time also be partially fluorinated. The total concentration of fluorinated organic compounds present in the fluid will typically be between 0.001 and 100 mg/l; the concentration of the added first adsorbent component will then usually be between 01 and 1000 mg/l, frequently 1 to 100 mg/l. Starting at concentrations of 0.2 mmol/l, frequently 1 to 10 mmol/l, depending on the first adsorbent component, an advantageous formation of micelles is to be expected. The concentration of the first adsorbent component will frequently be equally high or higher than that of the concentration of the fluorinated organic component to be separated, for example, at least 50 times to 1000 times as high (referred to the weight proportions). An at least substantial portion of adduct results from the interaction of the two components, wherein the stoichiometry of the adduct formed from the components depends on the concentration and on the chemical structure of the reactants. The contact time can comprise from seconds to hours, and is frequently within the range of 1 to 30 minutes.

The fluid is brought into contact with the second adsorbent component in step B), so that the formed adduct, as well as the portions of the still free contaminant and usually also of the first adsorbent component, are bonded to the second adsorbent component. This process typically occurs in a stirred tank reactor, as the second adsorbent component, for example, powdered activated carbon, is dispersed in the fluid (which has already been provided with the first adsorbent component) while stirring (approx. 100 rpm). The concentration of the introduced solid adsorbent component is between 1 and 10000 mg/l, preferably between 10 and 1000 mg/l; the stirring time can in turn comprise from 1 to 30 minutes. The adsorbent can alternatively be present in an adsorption column and be flowed through with the contaminated fluid in order to achieve the desired adsorption.

The next step includes the separation of the purified fluid from the loaded adsorbent by means of a flocculant. This process of solid and fluid separation is carried out in a stirred tank reactor; the flocculant is typically added at a concentration of 0.1-10 mg/l. It must be stirred for several minutes (approx. 100 rpm).

Sedimentation occurs without stirring after this step (even if no flocculant is added). The sediment is separated via a filtration device. The fluid purified in this way can, if necessary, be subjected to a further treatment with an adsorber, or also again go through the treatment according to the present invention.

According to the present invention, the object is furthermore attained by means of a kit for the separation of fluorinated organic compounds from contaminated fluids. This kit comprises a first adsorbent component, which is liquid, or can be brought into a liquid form, and a second (solid) adsorbent component. The first adsorbent component is a chemical compound having a lipophilic group and a hydrophilic group or containing such a compound in dissolved form, wherein the hydrophilic group contains at least one cationic group, and wherein the lipophilic group is selected form alkyl groups comprising at least one octyl unit, aryl groups and aralkyl groups. In this connection, that it can be brought into liquid form also means that this liquid form only occurs by the dissolution in the fluid to be purified or by dissolving in any other solvent that can be mixed with the fluid.

Further advantageous embodiments of the kit have been described above in the description of the method according to the present invention.

The object of the present invention is finally also attained by using a compound having the formulas $R^1$-E-L-X, $R^1$-L-E-X or the formula $R^1$-E-X for the separation of fluorinated organic compounds from contaminated fluids. In this connection, $R^1$, E, L and X are as defined above. In this regard, further advantageous embodiments have also been explained in the description of the method according to the present invention.

The method according to the present invention, the kit used therefore and also the compounds having the formulas $R^1$-E-L-X, $R^1$-L-E-X or the formula $R^1$-E-X used as a first adsorbent component are particularly suitable for the separation of fluorinated organic compounds. Fluorinated hydrocarbons, such as perfluorinated compounds, partially fluorinated surfactants or perfluorinated surfactants should be particularly mentioned in this connection. In this respect, it is also basically possible that a desorption of the adsorbed compounds (adduct) and therewith a regeneration of the separation phase (activated carbon) as well as the recovery of the fluorinated compounds is possible, in particular if they are valuable substances, which otherwise would have to be produced by means of expensive chemical reactions. Such a desorption can occur, for example, if weak alkaline amino groups are present in the first adsorbent component and form adducts with anions of, for example, perfluorinated surfactants. The acid anions of the surfactants are at the same time reversibly bonded, and the free amino groups are recovered with the addition of alkali during the regeneration. The pH value of the optimal regeneration is dependent on, or can be adjusted to, the type of the amino group (primary, secondary or tertiary amino group) and on the constitution of the adduct.

In summary, it should be pointed out that the new method especially draws on the prior art and the modern conditioning practice of PFT contaminated water and improves them by applying specific carrier compounds (according to the present invention: the first adsorbent component). The commercial adsorbents and their established regeneration means, such as thermal reactivation of activated carbon, can in this way continue to be used, and the materials used can at the same time be reduced, as well as the plant and processing costs be saved.

Further advantageous exemplary embodiments and further developments of the invention will be apparent below—without limitation to the generality—from the examples.

Adsorption in Batch Processing:

The adsorption in batch processing will be explained below, and the efficiency of the adsorption method will be shown using different reagents. In this connection, a four-step or six-step RRS system (stirred tank reactor sorption system) is used.

The process steps comprise:
Step 1: Dosage/Reagent 1: First adsorbent component
Step 2: Dosage/Reagent 2: Second adsorbent component
Step 3: Dosage/Reagent 3: Flocculant
Step 4: Sedimentation
Step 5: Dosage/Reagent 4: Second adsorbent component
Step 6: Sedimentation The used reagents and the number of steps vary for each example.

800 ml of PFT-containing raw water are measured with a measuring cylinder and presented in a 1000 ml beaker in each case. A total of four samples are prepared. An aqueous mixture containing the following PFT is used as PFT-containing raw water: perfluorooctane sulfonate (PFOS) 2.98 µg/l, perfluoroheptane sulfonate (PFHpS) 0.27 µg/l, perfluorohexane sulfonate (PFHxS) 3.90 µg/l, perfluorobutane sulfonate (PFBS) 0.54 µg/l, perfluorooctanic acid (PFOA) 0.36 µg/l, perfluoroheptanic acid (PFHpA) 0.13 µg/l, perfluorohexanic acid (PFHxA) 0.64 µg/l, perfluoropentanic acid (PFPeA) 0.21 µg/l, perfluorobutanic acid (PFBA) 0.23 µg/l.

The covered beakers are subsequently placed in the gang stirrer. As soon as the provided amount of the first adsorbent component (reagent 1) is fed to the respective beaker, the stirring blade is plunged into the medium, the stirrer is switched on, and the speed is set to the designated value.

The second adsorbent component (reagent 2) and the flocculant (reagent 3) are each dosed after the scheduled reaction times have ended. The speed of the stirrer is at the same time specifically adapted to the individual test phases. The sedimentation phase starts after the third step has ended. The stirrer is switched off for this purpose and the stirrer blades are removed from the samples.

After the sedimentation time has ended, the solids contained in the samples are separated by means of filtration. The filtrate is collected in 1000-ml beakers and the smallest possible sample volume is removed for further analysis (PFT concentration).

The stirrer blades and stirrer shafts of the gang stirrer are again cleaned, insofar as a further adsorption step (reagent 4) is carried out with the filtrate. After the second sedimentation time has ended, the sediment contained in the sample solution is separated by means of filtration and the remaining filtrate is again analyzed.

Example 1 a) Used Reagents:
Reagent 1: Production of 50 ml of reagent solution 49.5 g of distilled water and 0.5 g of Quab 342 (40% aqueous solution of 3-chloro-2-hydroxy-propyl dimethyl dodecyl ammonium chloride); Quab Chemical Company Inc., USA)
Reagent 2: Powdered activated carbon based on mineral coal (from Cornelsen Umwelttechnologie, Type: PFT Sorb, BET 900 m$^2$/g)
Reagent 3: Flocculant (from Ashland, Type: Praestol A4030L) production of 0.1% flocculant dosing solution of 99.9 g of distilled water and 0.1 g of flocculant
Reagent 4: like reagent 2 b) Process Steps and Settings:
Phase 1: Dosage of reagent 1, 1 ml/l each; speed: 200 min$^{-1}$ Reaction time: 30 minutes
Phase 2: Dosage of reagent 2; speed: 200 min$^{-1}$; reaction time: 30 minutes

|  | Preparation No. | | | |
| --- | --- | --- | --- | --- |
|  | 1 | 2 | 3 | 4 |
| Reagent 2 [mg/l] | 25 | 50 | 75 | 100 |

Phase 3: Dosage of reagent 3, 1 ml/l each; speed: initially 200 min$^{-1}$ after 1 minute 80 min$^{-1}$ reaction time: 30 minutes
Phase 4: Sedimentation; sedimentation time: 5 minutes
Phase 5: Filtration; filter type: Folded filter Whatman 597½
Phase 6: Dosage of reagent 4, dosage of reagent 1, 25 ml/l each; speed:
200 min$^{-1}$; reaction time: 30 minutes
Phase 7: Filtration; filter type: Folded filter Whatman 597½

Example 2

Implementation as described in Example 1, but using hydrolyzed 3-chloro-2-hydroxy-propyl dimethyl dodecyl ammonium chloride (degree of hydrolysis approx. 12 mol %) as reagent 1.

Example 3

Implementation as described in Example 1, but using (1-dodecyl)trimethyl ammonium chloride (from Alfa Aesar) as reagent 1.

Example 4

Implementation as described in Example 1, but using (1-tetradecyl)trimethyl ammonium chloride (from Alfa Aesar) as reagent 1.

Example 5 Test without the First Adsorbent Component

Implementation as described in Example 1; the same amount of distilled water is added instead of reagent 1.

Comparison of Examples 1 to 4 and Example 5

The comparison clearly shows how advantageous the method is according to the present invention. Table 1 shows the residual concentration of PFT in the filtrate in µg/l after having carried out the tests 1 to 5 (the blank tests are shown under concentration [conc.] PFTsorb=0):

TABLE 1

| Conc. PFTsorb [mg/l] | Concentration PFT [µg/l] | | | | |
|---|---|---|---|---|---|
| | Example 5 | Example 1 | Example 2 | Example 3 | Example 4 |
| 0 | 8.89 | 10.65 | 9.95 | 9.95 | 9.95 |
| 25 | 4.69 | 2.08 | 3.83 | 3.65 | 3.23 |
| 50 | 4.84 | 1.08 | 2.08 | 1.09 | 1.1 |
| 75 | 3.73 | 0.74 | 1.03 | 0.62 | 0.65 |
| 100 | 2.75 | 0.48 | 0.54 | 0.34 | 0.32 |
| 125 | 2.5 | | | | |
| 150 | 1.94 | | | | |
| 175 | 1.09 | | | | |
| 200 | 0.78 | | | | |

FIG. 1 shows the graphic preparation of the results obtained from the test series of Table 1. The activated carbon without the addition of the first adsorbent component (dashed line - - - ) shows the worst results. Example 1 (continuous line) shows the best results. Significantly lower amounts of adsorbent can also be used by adding chloro-2-hydroxy-propyl dimethyl dodecyl ammonium chloride. Example 2 (dot and dash line -•-•), Example 3 (dot and dash line) and Example 4 (dotted line) are between these results. FIG. 2 again illustrates this statement by applying the achieved degree of efficiency level depending on the ratio of adsorbent and PFT adsorbent.

Examples 6 to 10 Test Series without the First Adsorbent Component

Implementation as described in Example 1. Another second adsorbent component is used in an amount of 100 mg/l instead of powdered activated carbon. It is bone meal (powdered ground bovine bone with a raw ash content of 81.4%—Example 6), titanium oxide (powdered—Example 7), granular starch "Amylofax 75" from AVEBE (Example 8), granular starch "Wisprofloc P" from AVEBE (Example 9) and granular starch "Avecat 15" from AVEBE (Example 10). Compared to activated carbon, they have a more hydrophilic surface chemistry, as a result of which the degrees of efficiency for PFT adsorption are lower.

FIG. 3 shows the achieved degrees of efficiency of Examples 1 and 5 to 10 depending on the solid adsorbent component.

Example 11

Implementation as described in Example 1, but raw water is used with the ingredients according to the information in the following Table 2. Steps 3, 4 and 5 are furthermore omitted and step 1 is also omitted in the comparative tests with activated carbon 1 and 2. The adsorbent component 1 was finally used in an amount of 22.5 mg/l and the adsorbent component 2 was used in an amount of 100 mg/l.

Table 2 respectively shows two associated column pairs, in which the left column indicates the concentration of the respective PFT in raw water, and the right column indicates the amounts of this PFT separated by the absorbent component. It can be seen that a significantly better degree of efficiency can be achieved by means of the kit according to the present invention than with pure activated carbon.

TABLE 2

(all values are shown in µg/l)

| | Raw Water | Activated Carbon 1 | Raw Water | Activated Carbon 2 | Raw Water | Quab 342 + Activated Carbon 2 |
|---|---|---|---|---|---|---|
| PFBA | 0.56 | 0.09 | 0.46 | 0.18 | 0.65 | 0.52 |
| PFPeA | 1.6 | 0.81 | 1.4 | 1.01 | 1.9 | 1.86 |
| PFHxA | 2.2 | 1.88 | 2.1 | 2.03 | 3 | 3 |
| PFHpA | 0.4 | 0.39 | 0.43 | 0.43 | 0.48 | 0.48 |
| PFOA | 0.87 | 0.87 | 0.8 | 0.8 | 0.92 | 0.92 |
| PFBS | 1.00 | 0.90 | 0.96 | 0.96 | 1.1 | 1.1 |
| PFHxS | 6.40 | 6.35 | 4 | 4 | 7.6 | 7.6 |
| PFOS | 11 | 10.9 | 5.9 | 5.9 | 11 | 11 |
| PFT Sum | 24.03 | 22.19 | 16.05 | 15.31 | 26.65 | 26.48 |
| Degree of efficiency | | 92.3% | | 95.4% | | 99.4% |

Activated carbon 1=Donau Carbon, Hydraffin P1000

Activated carbon 2=Powdered activated carbon on the basis of mineral carbon (from Cornelsen Umwelttechnologie, Type: PFT Sorb, BET 1000 m$^2$/g)

Example 12

Implementation as described in Example 11 (also with regard to the used amounts of adsorbent components), but raw water is used with the ingredients according to the information of the following Table 3. Steps 3, 4 and 5 are also omitted, and step 1 is additionally omitted in the comparative examples with activated carbon 1 to 3 and step 2 is additionally omitted in the test "TEA Esterquat."

Table 3 shows the concentration of the respective PFT in raw water in the leftmost column, and the amounts of these PFTs separated by means of the adsorbent components are shown in the columns to the right thereof. It can be seen that the degree of efficiency almost achieved by means of the first adsorbent component without the additional solid adsorbent component is already that which is also achieved by means of the kit according to the present invention. If TEA esterquat is used, the activated carbon can already be omitted here because a precipitation of the formed adduct can be observed after this compound comes into contact with the raw water. The used TEA esterquat is an esterquat based on oleic acid, which can be obtained by means of triple esterification of triethanolamine with unsaturated C18 fatty acids (based on oleic acid) and subsequent quaternization with dimethyl sulfate. The solubility is 4 mg/l (at 20° C. and pH 7.1); the melting point is 4° C., and the density is 1.059 g/cm$^2$ (at 20° C.). The TEA esterquat is used as a solution in 2-propanol.

In any case, both examples have a significantly better degree of efficiency than it can be achieved with pure activated coal. In addition, it has been found that this effect is even more apparent, if only the PFTs with 6 or less carbon atoms in the fluoroalkyl group are taken into consideration.

TABLE 3

(all values are in µg/l)

| | Raw Water | Activated Carbon 1 | Activated Carbon 2 | Activated Carbon 3 | TEA Esterquat | TEA Esterquat + Activated Carbon 2 |
|---|---|---|---|---|---|---|
| PFBA | 6.9 | 0.5 | 0.5 | 0.7 | 0.8 | 0.9 |
| PFPeA | 16 | 4 | 4 | 3 | 4 | 5 |
| PFHxA | 33 | 6 | 11 | 4 | 12 | 12 |
| PFHpA | 5.5 | 2.5 | 4.1 | 1.6 | 4.1 | 3.9 |
| PFOA | 12 | 6.8 | 10.4 | 4.1 | 10.5 | 10.5 |
| PFNoA | 0.13 | 0.09 | 0.13 | 0.06 | 0.12 | 0.12 |
| PFDeA | 0.09 | 0.09 | 0.09 | 0.07 | 0.09 | 0.09 |
| PFOSA | 0.62 | 0.56 | 0.62 | 0.33 | 0.58 | 0.59 |
| PFBS | 31 | 13 | 16 | 7 | 24.5 | 23.6 |
| PFHxS | 170 | 112 | 150 | 60 | 160.6 | 160.7 |
| PFHpS | 24 | 21.1 | 23.39 | 16.2 | 23.59 | 23.61 |
| PFOS | 500 | 447 | 487 | 350 | 475 | 486 |
| 4:2 FTS | 0.25 | 0.21 | 0.24 | 0.17 | 0.21 | 0.21 |
| 6:2 FTS | 25 | 19.5 | 23.7 | 10 | 20.7 | 20.4 |
| 8:2 FTS | 13 | 12.32 | 12.85 | 9.6 | 12.49 | 12.57 |
| PFT Sum | 837.49 | 645.67 | 744.01 | 466.83 | 749.28 | 760.19 |
| Degree of efficiency | | 77.1% | 88.8% | 55.7% | 89.5% | 90.8% |
| C4-C6 Sum | 282.15 | 155.21 | 205.44 | 84.87 | 222.81 | 222.81 |
| C4-C6 Degree of efficiency | | 55.0% | 72.8% | 30.1% | 79.0% | 79.0% |

Activated carbon 3=Reagent 2

PFNoA=Perfluorononanoic acid, PFDeA=Perfluorodecanic acid, PFOSA=Perfluorooctanic acid amide, n:2 FTS=n:2 Fluorotelomer sulfonic acid $C_nF_{2n+1}C_2H_4SO_3H$ Example 13

Other compounds that are suitable as a first adsorbent component were tested without additionally using a solid adsorbent component. The addition of activated carbon can already be omitted, as in the case of the TEA esterquat (Example 12) because precipitation of the formed adduct can be observed after these compounds come into contact with raw water.

If the TEA esterquat of Example 12 is substituted under otherwise identical conditions with a solution of 80% dioleoyl ethyl-hydroxyethylmonium methosulfate in 20% glycol or alternatively with Tego Betaine F50 from Evonik (alkylamidopropyl betaine: 1-propanaminium-3-amino-N-carboxymethyl-N,N-dimethyl-N-$C_8$-$C_{18}$ acyl derivative), then precipitation products, which are different in type (flake structure) and amount, depending on the raw water and the first adsorbent component, are also observed with a variation of the used raw water. In any case, visually easy to perceive precipitation products and a clearly reduced residual PFT concentration have been found in the treated raw water.

The invention claimed is:

1. A kit for separation of fluorinated organic compounds from contaminated fluids, the kit comprising a first adsorbent component and a second adsorbent component, wherein the second adsorbent component is a solid adsorbent and the first adsorbent component is a chemical compound having a formula $R^1$-E-L-X, $R^1$-L-E-X or $R^1$-E-X, or includes a chemical compound having a formula $R^1$-E-L-X, $R^1$-L-E-X or $R^1$-E-X in dissolved form wherein $R^1$ is a lipophilic group including an alkyl group comprising at least one octylene unit, aryl groups, or aralkyl groups, wherein E is a hydrophilic group comprising at least one cationic group, the cationic group comprising an amine, an organic substituted ammonium, or a metal complex, wherein L is a linker, and X is a reactive group that chemically reacts with the contaminated fluid, or comprises hydroxy groups, wherein the first adsorbent component is furthermore present either in dissolved form or as a liquid, and wherein a flocculant is included in addition to the first and second adsorbent component.

2. A method for separation of fluorinated organic compounds from contaminated fluids by means of an adsorbent component comprising the following steps:

providing the adsorbent component, wherein the adsorbent component is a chemical compound comprising a lipophilic group and a hydrophilic group, or the adsorbent component comprises the chemical compound in dissolved form, wherein the hydrophilic group includes at least one cationic group, wherein the lipophilic group is selected from among alkyl groups comprising at least one octylene unit, aryl groups, or aralkyl groups, and wherein the at least one cationic group comprises an amine, an organic substituted ammonium, an organic substituted phosphonium, or a metal complex;

bringing the contaminated fluid into contact with the adsorbent component, wherein the contaminated fluid includes the adsorbent component at least partially in dissolved form; and separating the adsorbent component with an amount of adsorbed fluorinated organic compounds from the contaminated fluid.

3. The method of claim 2, wherein a flocculant is added prior to the separation of the adsorbent component with an amount of adsorbed fluorinated organic compounds from the contaminated fluid.

4. A method comprising:

separating a fluorinated organic compound from a contaminated fluid with an adsorbent compound having a formula $R^1$-E-L-X, $R^1$-L-E-X or a formula $R^1$-E-X, wherein R¹ is a lipophilic group selected from among alkyl groups comprising at least one octylene unit, aryl groups and aralkyl groups, E is a hydrophilic group including at least one cationic group, wherein the cationic group comprises an amine, an organic substituted ammonium, an organic substituted phosphonium or a metal complex, L is a linker, and X is a reactive group that chemically reacts with the contaminated fluid, or comprises hydroxy groups, wherein the hydroxy groups form hydrogen bonds with the contaminated fluid, wherein the contaminated fluid is brought into contact with said adsorbent compound so as to effect a formation of an adduct, wherein the adduct comprises the adsorbent compound with an adsorbed fluorinated organic compound, and the adsorbent compound with the adsorbed fluorinated organic compound is separated.

5. A method for separation of fluorinated organic compounds from contaminated fluids by means of a kit comprising at least a first adsorbent component and a second adsorbent component, the method comprising the following steps:
A) providing the first adsorbent component, wherein the first adsorbent component is a chemical compound comprising a lipophilic group and a hydrophilic group, or comprising such a compound in dissolved form, wherein the hydrophilic group comprises at least one cationic group,
wherein the lipophilic group is selected from among alkyl groups comprising at least one octylene unit, aryl groups and aralkyl groups, and
wherein the at least one cationic group comprises an amine, an organic substituted ammonium, an organic substituted phosphonium or a metal complex; and providing the second adsorbent component, wherein the second adsorbent component is a solid adsorbent;
B) bringing the contaminated fluid into contact with the first adsorbent component;
C) bringing the contaminated fluid into contact with the second adsorbent component; and
D) separating the at least first adsorbent component and the second adsorbent component with adsorbed fluorinated organic compounds from the contaminated fluid.

6. The method of claim 5, wherein steps B) and C) are carried out simultaneously, or step B) is carried out prior to step C).

7. The method of claim 5, wherein the first adsorbent component has a formula $R^1$-E-L-X, $R^1$-L-E-X or $R^1$-E-X, wherein $R^1$ is a lipophilic group, E is the hydrophilic group, L is a linker and X is a reactive group, which chemically reacts with the contaminated fluid in step B) and/or step C), or X includes hydroxy groups, wherein the hydroxy groups form hydrogen bonds with the contaminated fluid.

8. The method of claim 7, wherein the reactive group X has at least one hydroxy group, or at least one hydroxy group is formed on the reactive group X by a reaction of the reactive group X with the contaminated fluid.

9. The method of claim 8, wherein the reactive group X is selected from a group consisting of epoxide groups and groups that react to a hydroxy group in an $S_N$ reaction in step B) and/or step C).

10. The method of claim 9, wherein the reactive group X is selected from the group consisting of 2-chloroethanol groups, alkyl sulfonate groups, bromoalkyl groups, and iodoalkyl groups.

11. The method of claim 7, wherein two or more X or L-X groups are bonded to the hydrophilic group, and X is an ether group, or wherein at least one X or L-X group is bonded to the hydrophilic group, and X comprises a vicinal diol group or comprises a precursor for a vicinal diol group formed by reaction with the fluid in step B) and/or step C).

12. The method of claim 11, wherein the group X is an ethyl or methyl ether group bonded via a methylene, ethylene, or propylene linker in the first adsorbent component having the formula $R^1$-E-L-X, $R^1$-L-E-X, or $R^1$-E-X.

13. The method of claim 7, wherein a pH value of the contaminated fluid is changed as a result of the reaction of the reactive group X with the contaminated fluid.

14. The method of claim 13, Wherein the second adsorbent component provided in step A) has a non-ionic surface.

15. The method of claim 5, wherein the second adsorbent component is selected from a group consisting of activated carbon, aluminum oxides, silica gels, soot, zeolite, fibrous celluloses, and microcrystalline celluloses.

16. The method of claim 5, wherein a flocculent is added prior to step D).

17. The method of claim 5, wherein step B) and/or step C) are carried out in a stirred tank reactor.

* * * * *